(12) United States Patent
Atkins et al.

(10) Patent No.: US 7,834,223 B2
(45) Date of Patent: Nov. 16, 2010

(54) PROCESS FOR THE CONVERSION OF SYNTHESIS GAS TO OXYGENATES

(75) Inventors: Martin Philip Atkins, Middlesex (GB); Leslie William Bolton, Hampshire (GB); Benjamin Patrick Gracey, East Riding of Yorkshire (GB); John Glenn Sunley, East Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 252 days.

(21) Appl. No.: 11/920,724

(22) PCT Filed: May 18, 2006

(86) PCT No.: PCT/GB2006/001837

§ 371 (c)(1),
(2), (4) Date: Nov. 20, 2007

(87) PCT Pub. No.: WO2006/123158

PCT Pub. Date: Nov. 23, 2006

(65) Prior Publication Data

US 2009/0170966 A1    Jul. 2, 2009

(30) Foreign Application Priority Data

May 20, 2005    (EP) ................... 05253137

(51) Int. Cl.
*C07C 29/153* (2006.01)
*C07C 29/54* (2006.01)
*C07C 27/06* (2006.01)

(52) U.S. Cl. ...................... 568/885; 568/884

(58) Field of Classification Search ................... 568/880
See application file for complete search history.

(56) References Cited

U.S. PATENT DOCUMENTS

| 4,224,236 A | 9/1980 | Wunder et al. |
| 4,752,623 A | 6/1988 | Stevens et al. |
| 5,385,949 A | 1/1995 | Tierney et al. |
| 2005/0107482 A1 | 5/2005 | Van Egmond et al. |

FOREIGN PATENT DOCUMENTS

| DE | 25 03 204 | 7/1975 |
| EP | 0 033 212 | 8/1981 |
| EP | 0 180 719 | 5/1986 |
| EP | 550 242 | 12/1992 |
| GB | 1 413 929 | 11/1975 |

OTHER PUBLICATIONS

Beretta et al.: "Development of a Process for Higher Alcohol Production via Synthesis Gas," Ind. Eng. Chem. Res., pp. 3896-3908, 1998 American Chemical Society.
International Search Report mailed Oct. 31, 2006.
PCT Written Opinion of the International Searching Authority dated Oct. 31, 2006.
PCT Demand dated Dec. 15, 2006.
PCT International Preliminary Report on Patentability completed Apr. 12, 2007.

*Primary Examiner*—Brian J Davis
(74) *Attorney, Agent, or Firm*—Nixon & Vanderhye

(57) ABSTRACT

Process for the conversion of carbon oxide(s) and hydrogen containing feedstocks to oxygen-containing hydrocarbon compounds in the presence of a particulate catalyst, by reacting carbon oxide(s) and hydrogen in the presence of a particulate catalyst in a conversion reactor to form oxygen-containing hydrocarbon compounds. A saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms is added to the conversion reactor.

5 Claims, 1 Drawing Sheet

PROCESS FOR THE CONVERSION OF SYNTHESIS GAS TO OXYGENATES

This application is the U.S. national phase of International Application No. PCT/GB2006/001837 filed 18 May 2006 which designated the U.S. and claims priority to GB 05253137.3 filed 20 May 2005, the entire contents of each of which are hereby incorporated by reference.

This invention relates to an improved process for the conversion of carbon oxide(s) and hydrogen containing feedstocks to oxygen containing hydrocarbon compounds in the presence of a particulate catalyst.

In particular, the present invention relates to an improved process for the conversion of carbon oxide(s) (CO and CO2) and hydrogen containing feedstocks, e.g. synthesis gas or syngas, to alcohols in the presence of a particulate modified molybdenum sulphide based catalyst, or a modified methanol based catalyst and/or a modified Fischer-Tropsch catalyst.

BACKGROUND OF THE INVENTION

U.S. Pat. No. 4,122,110 relates to a process for manufacturing alcohols, particularly linear saturated primary alcohols, by reacting carbon monoxide with hydrogen at a pressure between 20 and 250 bars and a temperature between 150 DEG and 400DEG C., in the presence of a catalyst, characterized in that the catalyst contains at least 4 essential elements: (a) copper (b) cobalt (c) at least one element M selected from chromium, iron, vanadium and manganese, and (d) at least one alkali metal.

U.S. Pat. No. 4,831,060 relates to the production of mixed alcohols from carbon monoxide and hydrogen gases using a catalyst, with optionally a co-catalyst, wherein the catalyst metals are molybdenum, tungsten or rhenium, and the co-catalyst metals are cobalt, nickel or iron.

The catalyst is promoted with a Fischer-Tropsch promoter like an alkali or alkaline earth series metal or a smaller amount of thorium and is further treated by sulfiding. The composition of the mixed alcohols fraction can be selected by selecting the extent of intimate contact among the catalytic components.

Journal of Catalysis 114, 90-99 (1988) discloses a mechanism of ethanol formation from synthesis gas over CuO/ZnO/Al2O3. The formation of ethanol from CO and H2 over a CuO/ZnO methanol catalyst is studied in a fixed-bed microreactor by measuring the isotopic distribution of the carbon in the product ethanol when 13 C. methanol was added to the feed.

SUMMARY OF THE INVENTION

It is an object of the present invention to provide an improved process in term of selectivity and catalyst activity and operating life for the conversion of carbon oxide(s) and hydrogen containing feedstocks to oxygen containing hydrocarbon compounds in the presence of a particulate catalyst.

In particular, the present invention relates to an improved process in term of selectivity and catalyst activity and operating life for the conversion of carbon oxide(s) and hydrogen containing feedstocks, e.g. synthesis gas or syngas, to alcohols in the presence of a particulate modified molybdenum sulphide based catalyst, or a modified methanol based catalyst and/or a modified Fischer-Tropsch catalyst.

The present invention thus provides a process for the conversion of carbon oxide(s) and hydrogen containing feedstocks to oxygen containing hydrocarbon compounds in the presence of a particulate catalyst comprising the step of reacting carbon oxide(s) and hydrogen in the presence of a particulate catalyst in a conversion reactor to form oxygen containing hydrocarbon compounds characterized in that a saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms are added to the conversion reactor.

In particular, the present invention provides a process for the conversion of carbon oxide(s) and hydrogen containing feedstocks, e.g. synthesis gas or syngas, to alcohols in the presence of a particulate modified molybdenum sulphide based catalyst, or a modified methanol based catalyst and/or a modified Fischer-Tropsch catalyst comprising the step of reacting carbon monoxide and hydrogen in the presence of said catalyst in a conversion reactor to form alcohols characterized in that a saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms are added to the conversion reactor.

According to a preferred embodiment, the present invention provides a process for the conversion of hydrocarbon to alcohols comprising the steps of:
1. converting hydrocarbon to a mixture of carbon oxide(s) and hydrogen in a syngas reactor,
2. passing the mixture of carbon oxide(s) and hydrogen from the syngas reactor to a conversion reactor, and
3. reacting said mixture in said conversion reactor in the presence of a particulate modified molybdenum sulphide based catalyst, and/or a modified methanol based catalyst and/or a modified Fischer-Tropsch catalyst to form alcohols, characterised in that a saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms are added to the conversion reactor.

For the purpose of the present invention and appended claims, producing oxygen containing hydrocarbon compounds from mixture of carbon oxide(s) and hydrogen (e.g. synthesis gas) means that the hydrocarbon oxygenates represent at least 10% by weight of the products obtained from the conversion reactor, preferably at least 20% by weight, more preferably at least 40% by weight.

According to a preferred embodiment of the present invention, the oxygen containing hydrocarbon compounds are alcohols, mainly methanol, propanol, ethanol and butanols (predominately n-butanol and isobutanol); said methanol, propanols (predominately n-propanol with low amounts of iso-propanol) ethanol and butanol preferably represent together at least 10% by weight of the products obtained from the conversion reactor, more preferably at least 20% by weight, most preferably at least 40% by weight.

According to another embodiment of the present invention, water and carbon dioxide are also produced in the conversion reactor; then, water and alcohols preferably represent together at least 80% by weight of the nett products obtained from the process.

According to a preferred embodiment of the present invention, the saturated monocarboxylic acid having from 1 to 3 carbon atoms and/or the ester of a saturated monocarboxylic acid having from 1 to 3 carbon atoms with a monohydric aliphatic paraffinic alcohol having from 1 to 4 carbon atoms which are added to the conversion reactor comes from the oxygenates obtained from the conversion reactor as by-products. Said saturated monocarboxylic acid having from 1 to 3 carbon atoms and/or ester of a saturated monocarboxylic acid having from 1 to 3 carbon atoms with a monohydric aliphatic paraffinic alcohol having from 1 to 4 carbon atoms are thus preferably separated from the alcohols produced in the conversion reactor and sent back to the said conversion reactor.

According to another preferred embodiment of the present invention, the saturated monocarboxylic acid having from 1 to 3 carbon atoms and/or the ester of a saturated monocarboxylic acid having from 1 to 3 carbon atoms with a monohydric aliphatic paraffinic alcohol having from 1 to 4 carbon atoms which are added to the conversion reactor are preferably selected from methyl acetate or ethyl acetate or a mixture thereof.

Quite surprisingly, the addition and/or recycle of even tiny amounts of saturated monocarboxylic acid having from 1 to 3 carbon atoms and/or ester of a saturated monocarboxylic acid having from 1 to 3 carbon atoms with a monohydric aliphatic paraffinic alcohol having from 1 to 4 carbon atoms to the conversion reactor have proven to be highly beneficial to the alcohols selectivity, especially the ethanol selectivity, while simultaneously increasing catalyst activity and improving operating life.

Beyond these unexpected advantages, other advantages have also been found when applying the present process invention, amongst others:
  (i) less waste, less by-products and thus higher carbon efficiency.
  (ii) less capital, fewer separations, reduced storage tanks.
  (iii) alcohol product free from esters suitable for dehydration. Though esters can be dehydrated to carboxylic acid and olefin, the presence of carboxylic acids adds complexity to the process and may cause additional corrosion duty
  (iv) no corrosion and metallurgy constraints due to the potential hydrolysis of the esters during subsequent purification and storage stages As indicated, the particulate catalyst used in the conversion reactor is preferably a modified molybdenum sulphide based catalyst, and/or a modified methanol based catalyst and/or a modified Fischer-Tropsch catalyst.

Preferably, the catalyst used in the present invention contains at least molybdenum and/or copper; it is preferably promoted by the addition of an alkali metal salt. Molybdenum sulphide based catalysts are preferred; a salt of potassium, especially potassium carbonate, is the preferred promoter.

Most preferably, the catalyst used is a molybdenum sulphide based catalysts containing cobalt, the molybdenum to cobalt molar ratio being preferably comprised between 1.5 and 2.5, more preferably 2; the said molybdenum sulphide based catalysts containing cobalt is most preferably promoted with potassium carbonate.

According to an embodiment of the present invention, the catalyst used in the conversion reactor does not produce any acid and/or ester compound. Thus, according to another embodiment of the present invention, the acid and/or ester compound added to the conversion reactor does not come from the recycling of a compound produced in the said conversion reactor.

The hydrocarbon feedstock used for syngas generation is preferably a carbonaceous material, for example biomass, plastic, naphtha, refinery bottoms, smelter off gas, municipal waste, coal and/or natural gas, coal and natural gas being the preferred ones, most preferably natural gas.

Processes for producing mixtures of carbon oxide(s) and hydrogen (synthesis gas) are well known. Each has its advantages and disadvantages and the choice of using a particular reforming process is dictated by economic and available feed stream considerations, as well as by the desired mole ratio of H2:CO in the feedstock resulting from the reforming reaction. The synthesis gas may be prepared using any of the processes known in the art including partial oxidation of hydrocarbons, steam reforming, gas heated reforming, microchannel reforming (as described in, for example, U.S. Pat. No. 6,284,217 which is herein incorporated by reference), plasma reforming, autothermal reforming and any combination thereof. A discussion of these synthesis gas production technologies is provided in "Hydrocarbon Processing" V78, N.4, 87-90, 92-93 (April 1999) and "Petrole et Techniques", N. 415, 86-93 (July-August 1998). It is also envisaged that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187-196. Alternatively, the synthesis gas may be obtained by short contact time catalytic partial oxidation of hydrocarbonaceous feedstocks as described in EP 0303438. Preferably, the synthesis gas is obtained via a "Compact Reformer" process as described in "Hydrocarbon Engineering", 2000, 5, (5), 67-69; "Hydrocarbon Processing", 79/9, 34 (September 2000); "Today's Refinery", 15/8, 9 (August 2000); WO 99/02254; and WO 200023689.

Any hydrocarbon-containing feed stream that can be converted into a feedstock comprising carbon monoxide and hydrogen, most preferably a synthesis gas (or "syngas"), is useful in the processes of the invention. The ratio of hydrogen to carbon monoxide in the reaction zone is preferably in the range of 20:1 to 0.1:1 by volume, more preferably in the range of 5:1 to 0.2:1, most preferably in the range of 1.5:1 to 0.5:1, e.g. 1:1. The alcohol synthesis catalysts can also catalyze the water gas shift reaction. A consequence of this is that hydrogen and carbon dioxide are interconvertable with carbon monoxide and water. For high partial pressures of carbon dioxide (at or above the water gas shift equilibrium), carbon dioxide can act as a carbon monoxide source and a hydrogen sink and this can effect the apparent preferred syngas ratio. Useful feed streams include natural gas (mainly methane, but natural gas composition can vary depending on location and source), naphtha, refinery off-gas, LPG, gas oil, vacuum residuals, shale oils, asphalts, various types of fuel oils, coal based/lignin deposits and hydrocarbon containing process recycle streams. According to a preferred embodiment of the present invention, methane is used as the hydrocarbon-containing feed stream to be converted into carbon oxides(s) and H2.

Feedstocks comprising carbon monoxide and hydrogen, e.g., synthesis gas may undergo purification prior to being fed to any reaction zones. Synthesis gas purification may be carried out by processes known in the art. See, for example, Weissermel, K. and Arpe H.-J., Industrial Organic Chemistry, Second, Revised and Extended Edition, 1993, pp. 19-21.

The particular reaction conditions for the conversion reactor embodiments described below are not narrowly critical and can be any effective reaction conditions sufficient to produce mainly oxygen containing hydrocarbon compounds. The exact reaction conditions will be governed by the best compromise between achieving high catalyst selectivity, activity, lifetime and ease of operability, as well as the intrinsic reactivity of the starting materials in question and the stability of the starting materials and the desired reaction product to the reaction conditions.

In one embodiment of this invention, feedstock comprising the desired molar ratio of H2:CO is fed to a conversion reactor at a controlled rate and the reaction is carried out in a reaction zone under controlled conditions of temperature and pressure in the presence of a catalyst to convert the feedstock into oxygenates. The temperature in the reaction zone is selected from the range of from about 150° C. to about 400° C., preferably a temperature in the range of from about 200° C. to about 350° C. and most preferably from 250-330° C. The gas hourly space velocity (GHSV) of the feedstock (liters of feedstock/hr/liter of catalyst) passing through the reaction zone can vary significantly, depending upon a variety of factors such as, for example, reaction conditions, composition of the feedstock and quantity and type of catalyst being used. The GHSV can be maintained at any rate in the range of from about 1 to about 30,000 hr-1 or more, preferably will be maintained at a rate of at least about 500 hr-1, and more preferably will be maintained at a rate of at least 1,000 hr-1. The pressure in the conversion reaction zone may be selected from the range of from about 5 to 200 bar, preferably a pressure in the range of from about 50 to 150 bar and most preferably at 80-120 bar. The hydrogen and carbon monoxide partial pressures should be sufficient to enable the production of oxygenates. Hydrogen and carbon monoxide may be fed separately to the conversion reactor or, preferably in combination, e.g., as synthesis gas.

For purposes of this invention, GHSV is gas hourly space velocity which is the rate of gas flow over the catalyst. It is determined by dividing the volume of gas (at 25° C. and 1 atmosphere) which passes over the catalyst in one hour by the volume of the catalyst. LHSV is liquid hourly space velocity which is the rate that the liquid organic substrate is fed to the conversion reactor. It is determined by dividing the liquid volume pumped in one hour by the volume of catalyst.

The conversion to oxygenates reaction can be carried out by passing the mixture of hydrogen and carbon monoxide over the conversion catalyst as a vapor phase reaction or as a liquid phase reaction, e.g., slurry reaction or trickle bed fluidized bed reactor.

The reaction may be carried out in any appropriate reactor, e.g. a tubular reactor using a fixed bed of the catalyst. The reactants may be fed to the catalyst by feeding down or up, or a combination of both, to a fixed bed located in a tubular reactor. It may be desirable to use a reactor design that operates by plug flow and causes minimal turbulence in the reactor zone. The reaction may be effected in a dynamic bed of the catalyst. In such a reaction, the bed of catalyst is moving such as in the case of a fluid bed of the catalyst. The alcohols conversion reactor may preferably be chosen amongst tubular, multitubular, slurry, moving bed, fluidized bed, radial bed, multibed or reactive distillation reactor. It is preferably a multibed or multitubular vapor phase reactor.

BRIEF DESCRIPTION OF THE DRAWING

The invention is further illustrated with reference to the accompanying FIG. 1 which is a schematic of the process of the invention.

EXAMPLE

Catalyst Preparation

Figure 1:
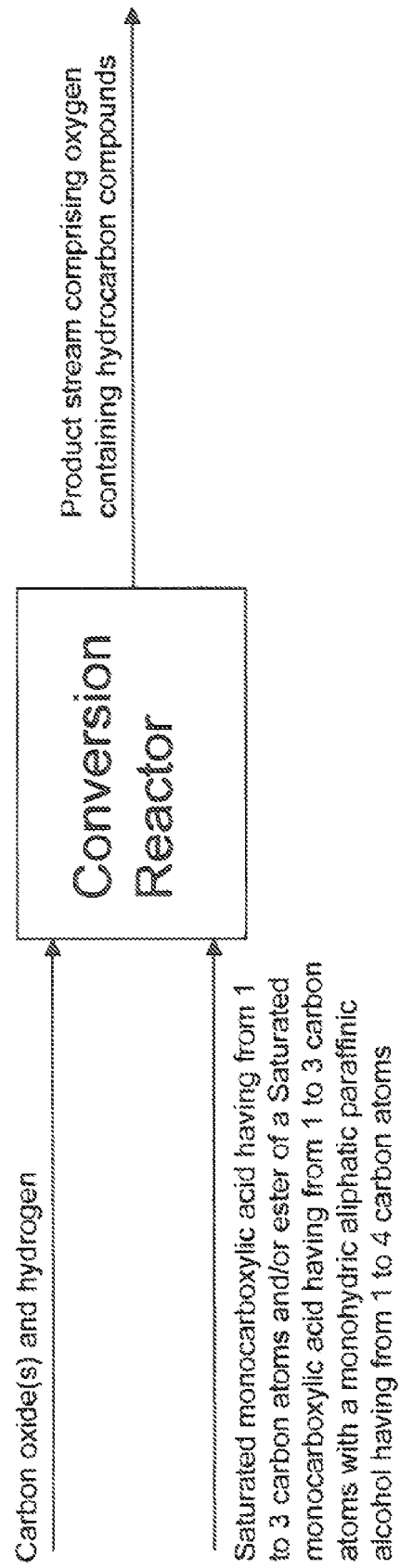

A cobalt/molybdenum sulphide catalyst was prepared by co-precipitation.

1. Preparation of Solution A 30 g of ammonium molybdate tetrahydrate was dissolved in 212 $cm^3$ of 22 wt % ammonium sulfide aqueous solution and stirred for 1 hour at 60° C.

2. Preparation of Solution B 21 g of Cobalt Acetate was dissolved in 400 $cm^3$ of dionised water.

3. Preparation of cobalt/molybdenum sulphide precipitate C

Solutions A and B were transferred into two separate dropping funnels. The 2 solutions were simultaneously added dropwise to a stirred solution of 30 wt % aqueous acetic acid (200 $cm^3$) over a 1 hour period, the temperature was kept constant at 50° C. The precipitate C in acetic acid was allowed to stir for a further 1 hour before filtering under vacuum. The filtrate was dried at room temperature for 18 hours and was subsequently calcined in a furnace at 500° C. under an atmosphere of nitrogen for 1 hour.

The catalyst was prepared by grinding 6.6 g of the calcined precipitated cobalt/molybdenum sulphide with 2 g Bentonite clay and 1 g $K_2CO_3$.

Catalyst Testing

The catalyst (9.6 g) was loaded into a tubular reactor (15 mm internal diameter) and a carborundum pre-heat mixing zone (20 $cm^3$) loaded upstream of the catalyst and brought to 200deg C. in 100 BarG nitrogen. The catalyst is then brought to a reaction temperature of 310° C. (~1deg C./min) in 1:1 $CO:H_2$ gas at 100 barg pressure at a flow rate giving a gas hourly space velocity (GHSV, defined as volume flow of reactant gas at STP per volume of catalyst per hour) of ~1300 $h^{-1}$ (The actual flow rates are 108.9 mlmin-1 CO and 108.7 mlmin-H2). The reaction products were analyzed by an on-line Gas Chromatogram (CP9001-80-100 Mesh Carbosieve SII and 0.25 micron Innowax columns). The reaction was allowed to run for 125 hours on stream after which point a 5 mol % flow of methanol was fed to the reactor, after 240 hours on stream an additional 2 mol % flow of methyl acetate was added to the reactor.

The results of the experiment (Table 1) demonstrate that on addition of methyl acetate to the reactor feed a significant improvement in EtOH productivity relative to propanol and methane productivities is achieved.

TABLE 1

| Feed | Time on Stream (hours) | Average Ratio g/hr EtOH/g/hr PrOH | Average Ratio g/hr EtOH/g/hr CH4 |
|---|---|---|---|
| CO/H2 | 125-190 | 1.42 | 1.95 |
| CO/H2 + 5 mol % MeOH | 191-239 | 1.70 | 1.03 |
| CO/H2 + 5% MeOH + 2% MeOAc | 240-330 | 2.64 | 1.65 |

The invention claimed is:

1. Process for the conversion of carbon oxide(s) and hydrogen containing feedstocks to alcohols in the presence of a particulate catalyst comprising at least molybdenum, copper or mixtures thereof, comprising the steps of:
   reacting carbon oxide(s) and hydrogen in the presence of said particulate catalyst in a conversion reactor to form alcohols; and
   adding a saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms to the conversion reactor.

2. Process for the conversion of hydrocarbon to alcohols comprising the steps of:

a. converting hydrocarbon to a mixture of carbon oxide(s) and hydrogen in a syngas reactor,
b. passing the mixture of carbon oxide(s) and hydrogen from the syngas reactor to a conversion reactor,
c. reacting said mixture in said conversion reactor in the presence of a particulate catalyst which comprises at least molybdenum, copper or mixtures thereof to form alcohols, and adding a saturated monocarboxylic acid having from 1 to 3 carbon atoms and/or an ester of a saturated monocarboxylic acid having from 1 to 3 carbon atoms with a monohydric aliphatic paraffinic alcohol having from 1 to 4 carbon atoms to the conversion reactor.

3. Process according to claim 1, wherein the saturated monocarboxylic acid having from 1 to 3 carbon atoms and/or the ester of a saturated monocarboxylic acid having from 1 to 3 carbon atoms with a monohydric aliphatic paraffinic alcohol having from 1 to 4 carbon atoms which are added to the conversion reactor are selected from the group consisting of methyl acetate, ethyl acetate and a mixture thereof.

4. Process according to claim 1, wherein the saturated monocarboxylic acid having from 1 to 3 carbon atoms and/or the ester of a saturated monocarboxylic acid having from 1 to 3 carbon atoms with a monohydric aliphatic paraffinic alcohol having from 1 to 4 carbon atoms which are added to the conversion reactor comes from the oxygenates obtained from the conversion reactor as by-products.

5. Process according to claim 4 wherein said saturated monocarboxylic acid having from 1 to 3 carbon atoms and/or ester of a saturated monocarboxylic acid having from 1 to 3 carbon atoms with a monohydric aliphatic paraffinic alcohol having from 1 to 4 carbon atoms are separated from the alcohols.

* * * * *